(12) United States Patent
Jaffarullah et al.

(10) Patent No.: US 9,205,467 B2
(45) Date of Patent: Dec. 8, 2015

(54) ROBOTIC VEHICLE FOR HOLIDAY TESTING OF COATING ON STORAGE TANK BASE PLATES

(71) Applicant: Saudi Arabian Oil Company, Dhahran (SA)

(72) Inventors: Kma M. Jaffarullah, Yanbu (SA); Fahad A. Al-Wehebi, Yanbu (SA); Mohammed Ahmed Baageel, Yanbu (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 13/740,951

(22) Filed: Jan. 14, 2013

(65) Prior Publication Data

US 2014/0196969 A1 Jul. 17, 2014

(51) Int. Cl.
| | |
|---|---|
| *B08B 5/04* | (2006.01) |
| *B08B 1/00* | (2006.01) |
| *B08B 3/02* | (2006.01) |
| *G05D 1/00* | (2006.01) |
| *G01N 33/00* | (2006.01) |

(52) U.S. Cl.
CPC ... *B08B 5/04* (2013.01); *B08B 1/00* (2013.01); *B08B 3/024* (2013.01); *G05D 1/00* (2013.01); *G01N 33/00* (2013.01)

(58) Field of Classification Search
CPC .......... G01N 33/00; B63B 59/00; B08B 5/04; B08B 1/00; B08B 3/024
USPC .................................................. 180/200, 22
See application file for complete search history.

(56) References Cited

U.S. PATENT DOCUMENTS

| | | | |
|---|---|---|---|
| 3,106,677 A * | 10/1963 | Lenville .................... | 324/559 |
| 3,198,541 A * | 8/1965 | Christenson et al. ......... | 180/409 |
| 4,621,562 A * | 11/1986 | Carr et al. .................... | 89/41.05 |
| 4,890,567 A * | 1/1990 | Caduff .......................... | 114/222 |
| 4,946,570 A * | 8/1990 | Kumar ........................ | 204/196.3 |
| 4,962,360 A * | 10/1990 | Homma et al. ............... | 324/700 |
| 5,350,033 A * | 9/1994 | Kraft ............................. | 180/167 |
| 6,832,183 B1 * | 12/2004 | Barich et al. ................... | 703/22 |
| 7,285,203 B2 * | 10/2007 | Russell et al. ................ | 205/725 |
| 2013/0014598 A1 * | 1/2013 | Langley et al. ............. | 73/865.8 |
| 2013/0099815 A1 * | 4/2013 | Kim et al. ................ | 324/756.03 |

* cited by examiner

*Primary Examiner* — Joseph Rocca
*Assistant Examiner* — Michael Stabley
(74) *Attorney, Agent, or Firm* — Abelman, Frayne & Schwab

(57) ABSTRACT

A robotic holiday testing apparatus for detecting and marking holidays in the protective coating atop a metal base plate of a storage tank, including:
  a. a vehicle,
  b. a power drive unit selectively coupled to a first set of wheels to move the vehicle in the forward or backward direction, and to a second set of wheels to move the vehicle and the right or left direction,
  c. a holiday detection apparatus having a wettable sponge electrical contact element for establishing an electric circuit with the base plate through each of the holidays,
  d. a tank for containing an electrolytic fluid supplied into the wettable sponge, and
  e. a controller which selectively operates the power drive unit to:
    move the vehicle in the forward direction for selected distance, and
  f. to move the vehicle in the left or right direction for selected distance,
the vehicle thus being movable along a path while the holiday testing apparatus thereon detects and marks holidays for subsequent repair.

13 Claims, 13 Drawing Sheets

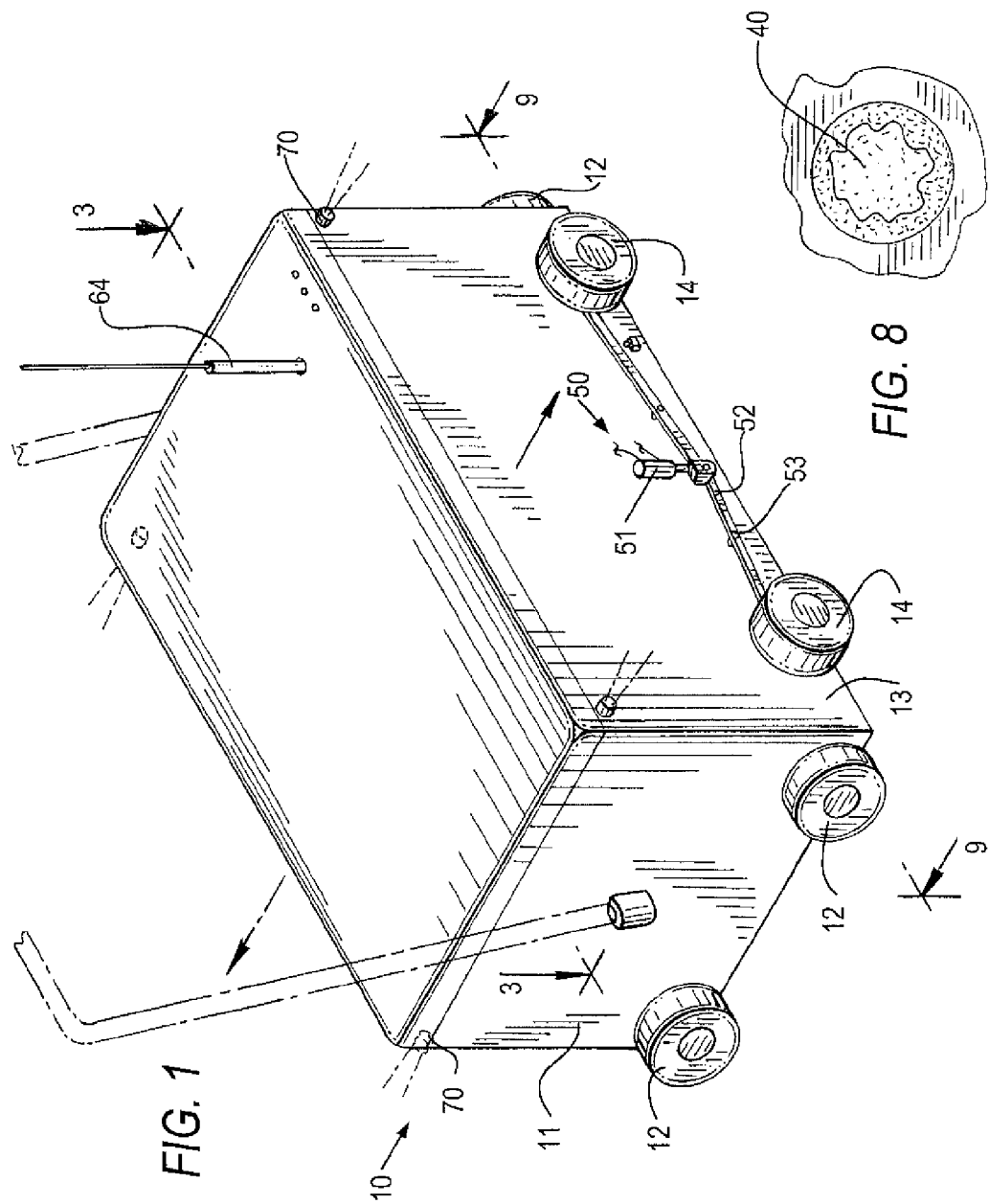

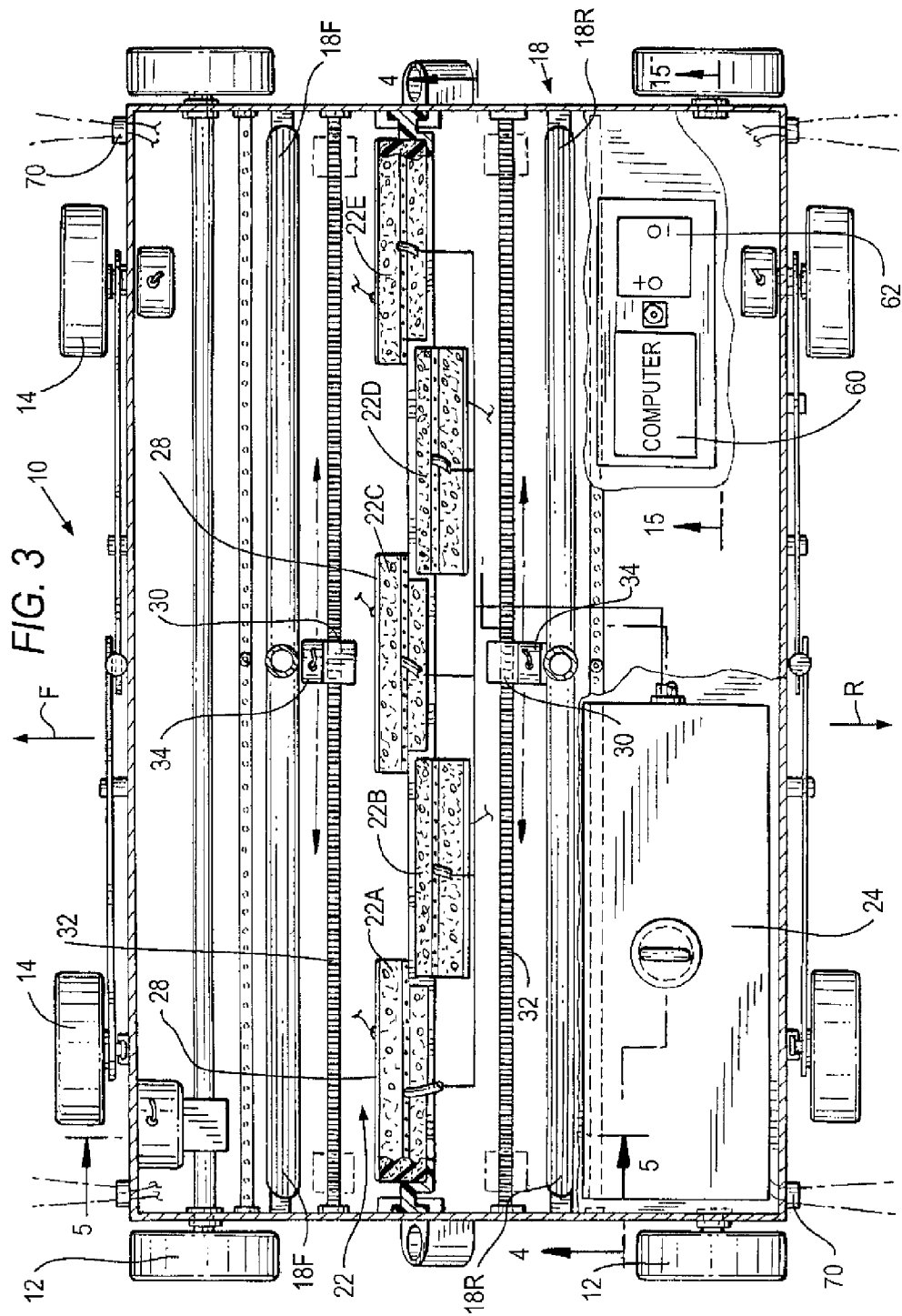

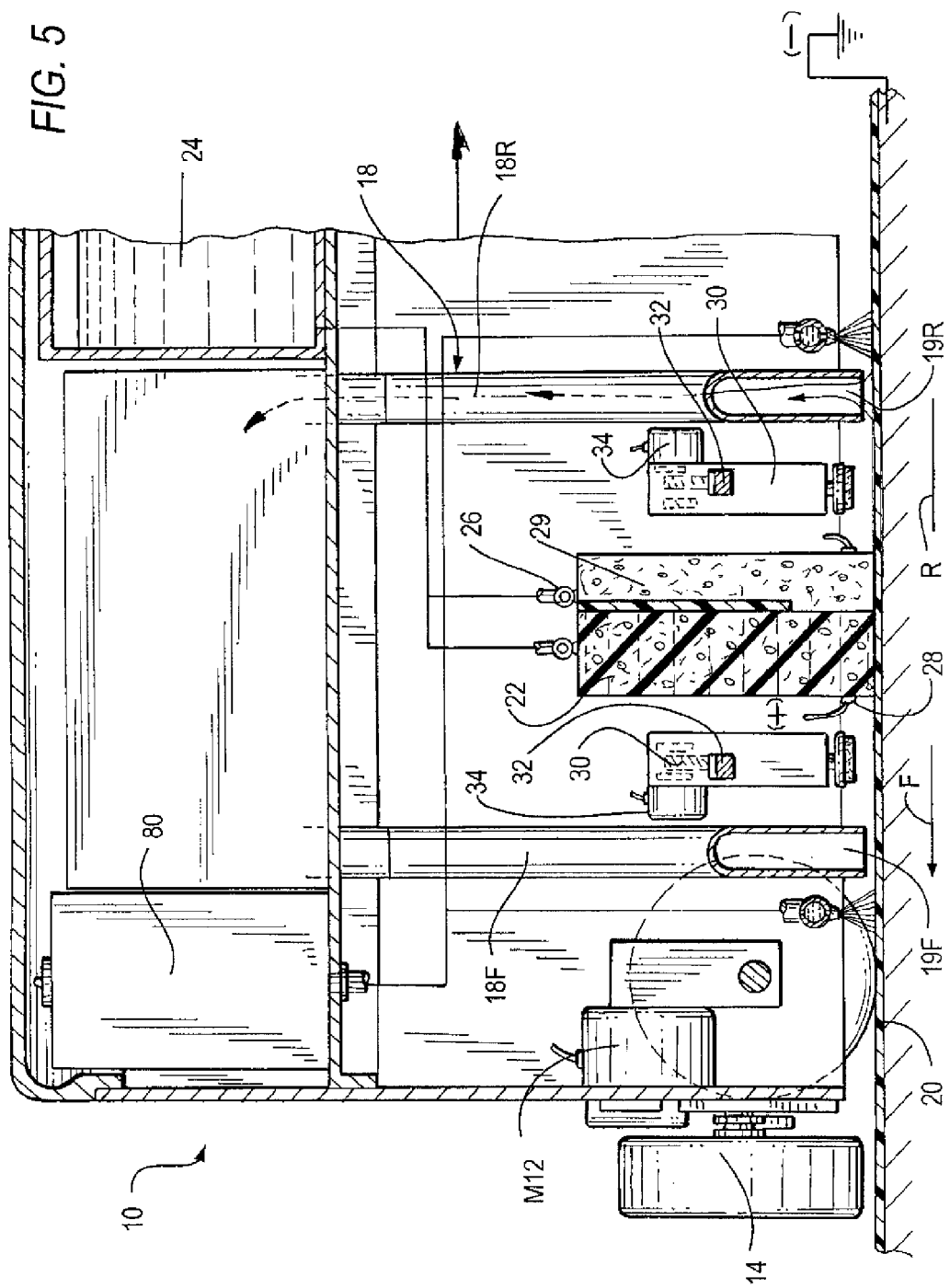

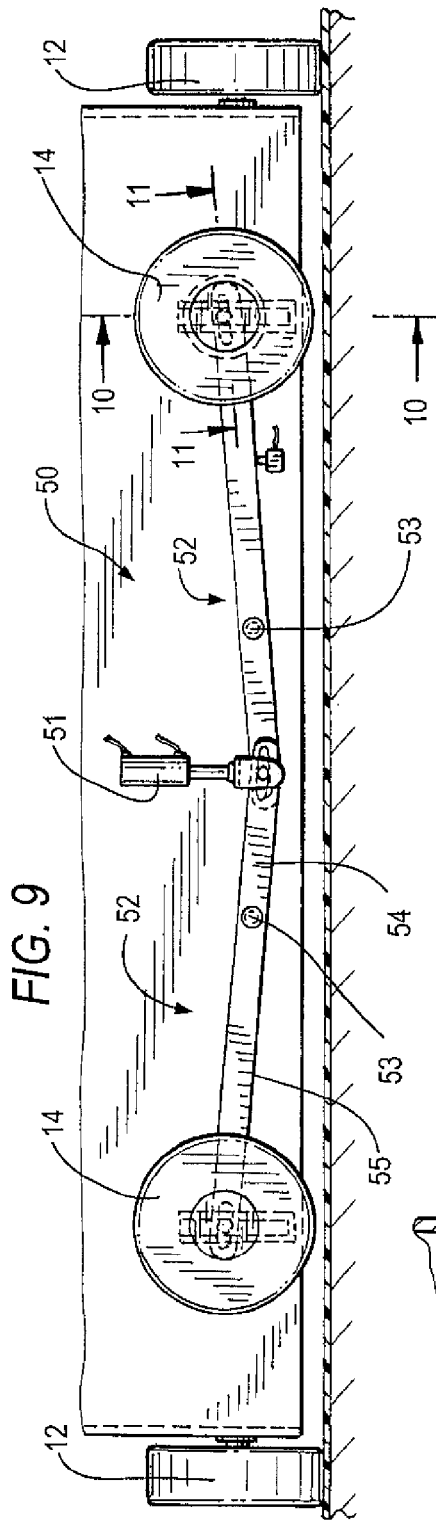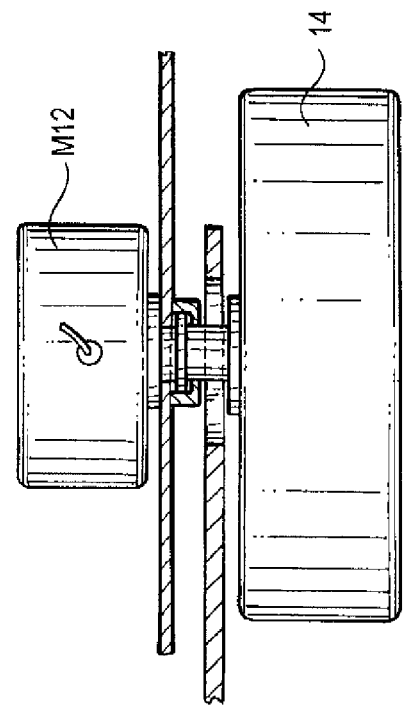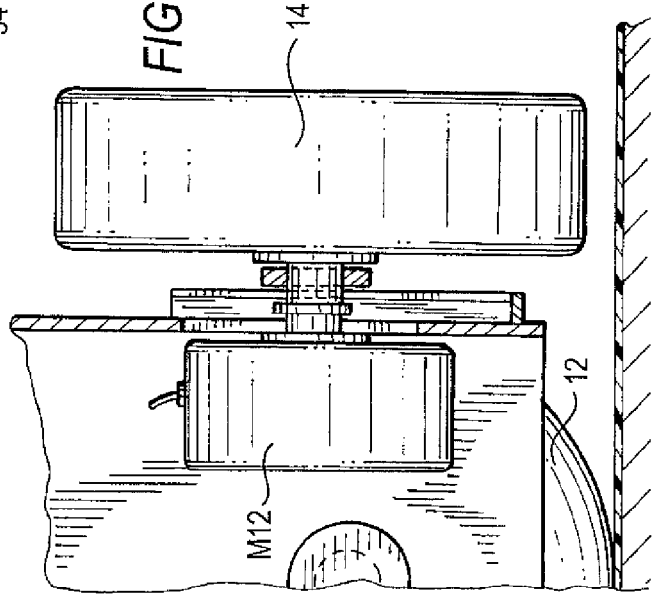

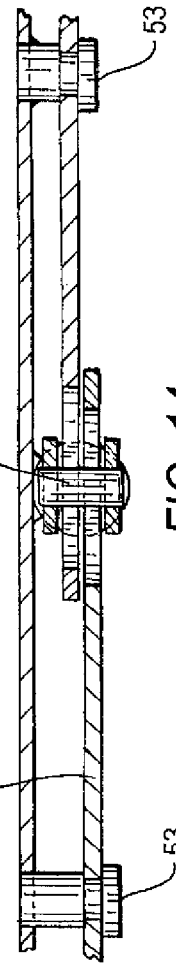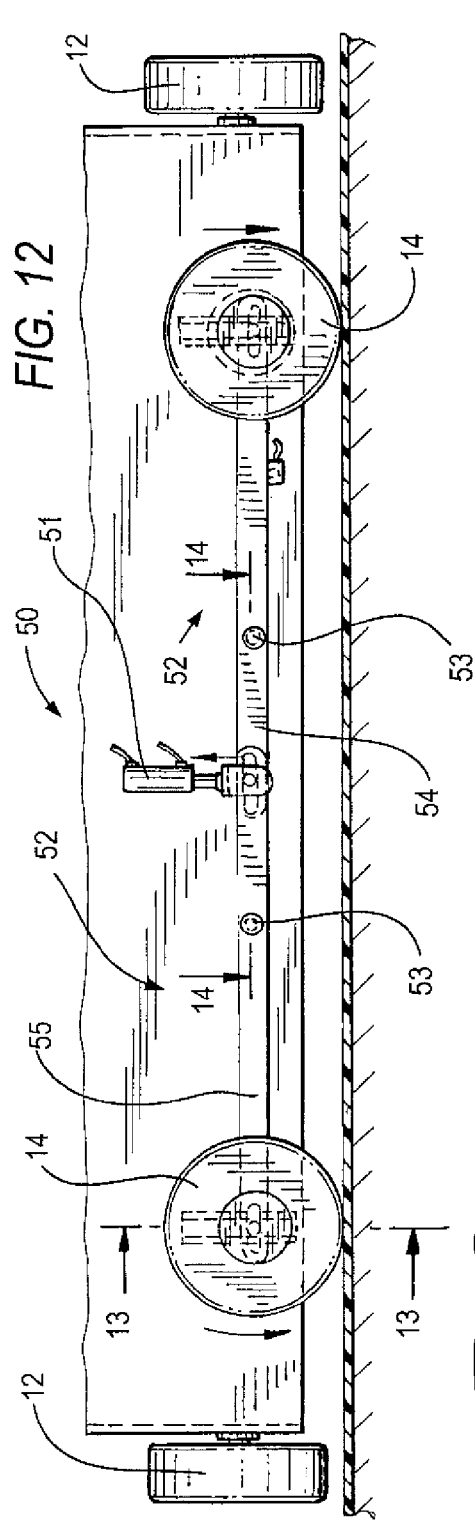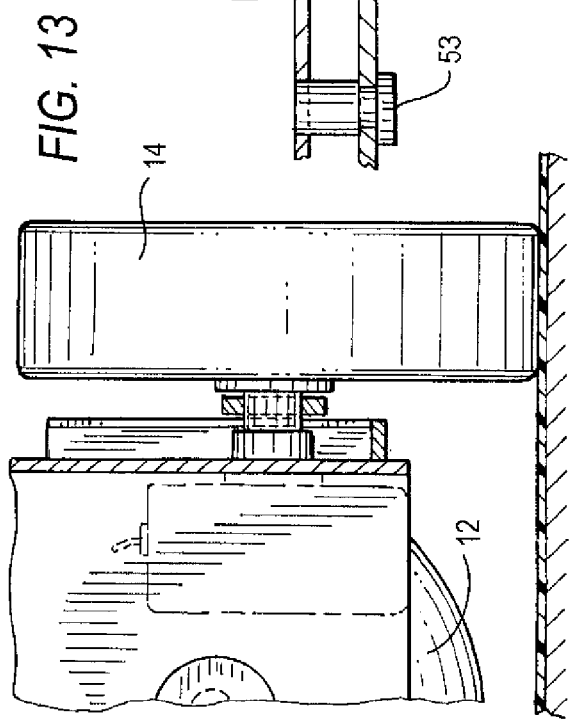

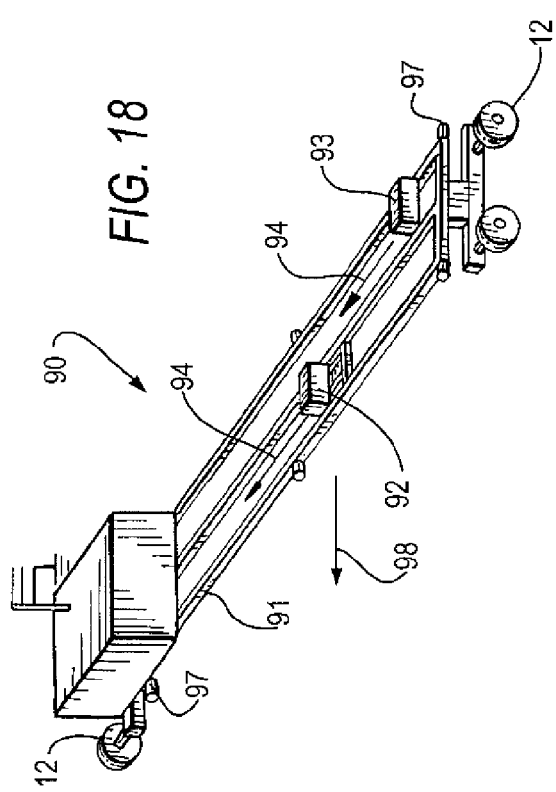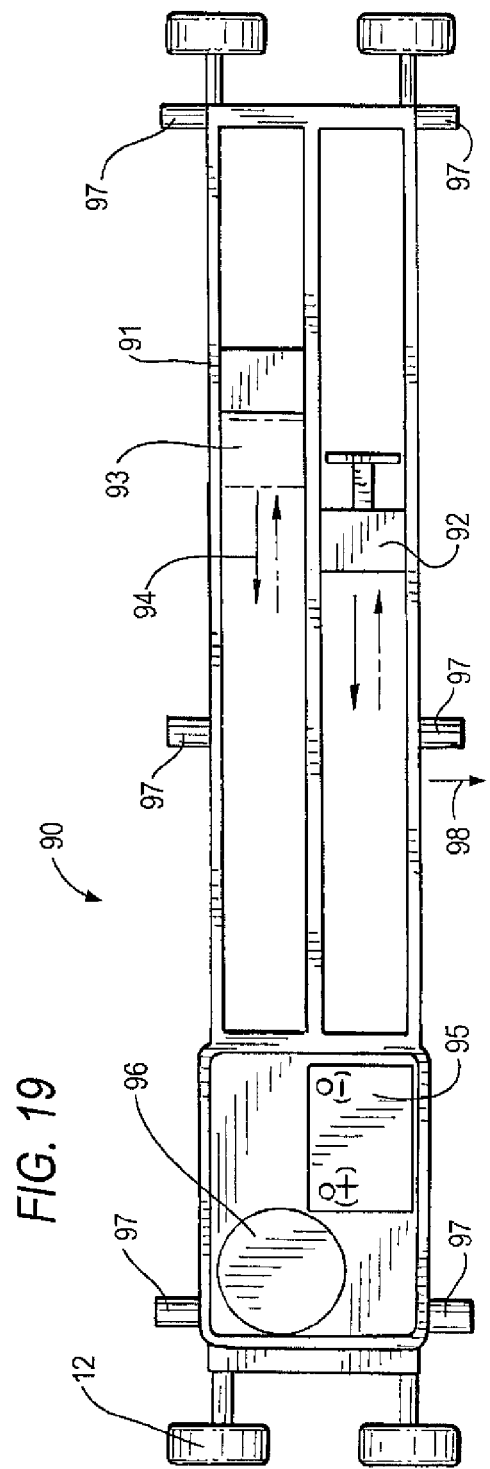

ROBOTIC VEHICLE FOR HOLIDAY TESTING OF COATING ON STORAGE TANK BASE PLATES

I. FIELD OF THE INVENTION

Figures 2A, 2B:
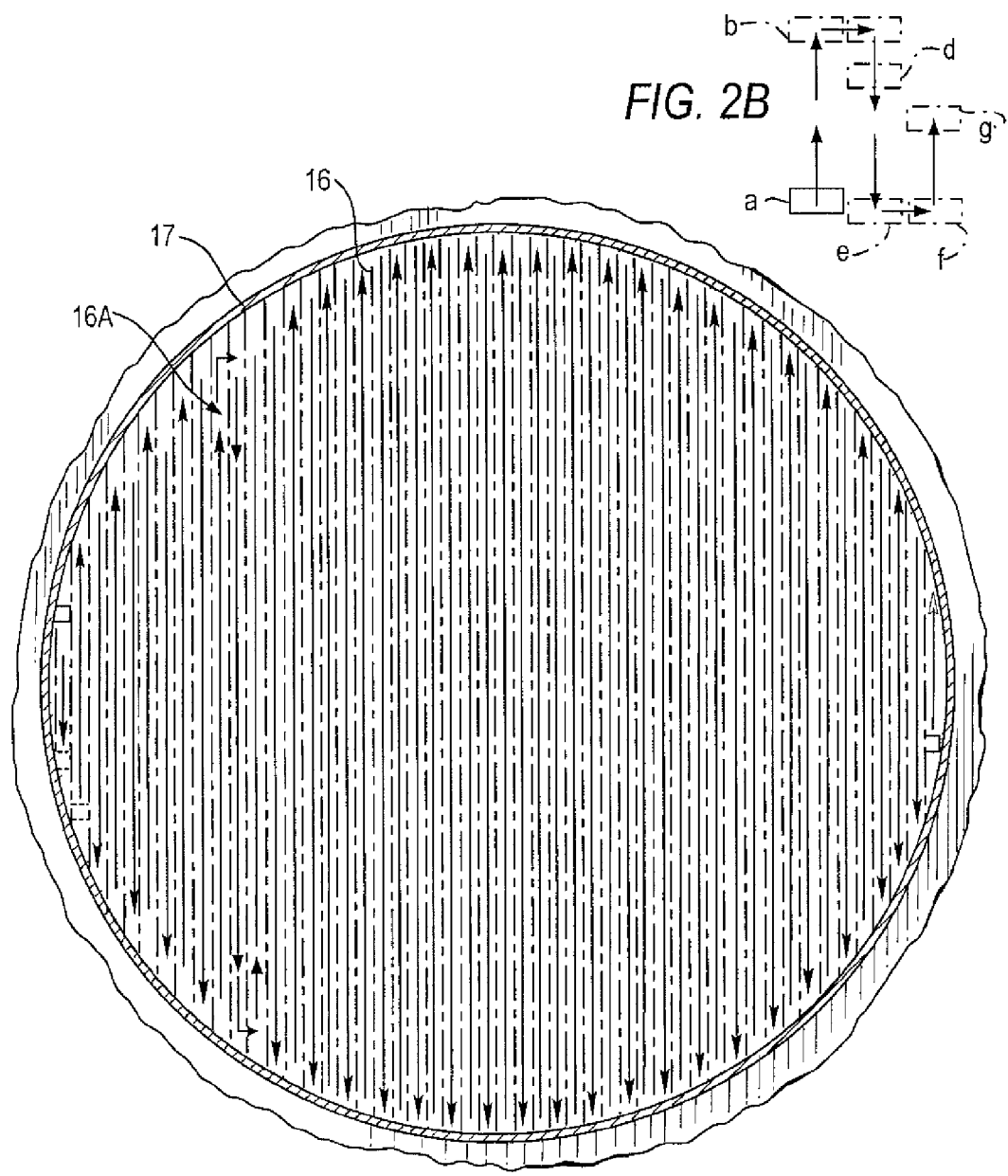

The present invention is in the field of detecting and repairing holidays in the coating on a base plate of a storage tank, and more particularly detecting and repairing such holidays in a storage tank containing liquid petroleum products.

II. BACKGROUND AND PRIOR ART

Holiday detectors also known as porosity detectors, spark testers, porosimeters or pinhole detectors are employed in the non-destructive detection of apertures or thin points in protective coatings on surfaces of metal pipes and storage tank base plates susceptible to corrosion from fluid in contact with such surfaces. These detectors may be operated with a stationary power supply or a battery carried by the detector.

For the present invention relevant holiday testers employ for the contact element a brush or sponge into which is directed and electrolytic solution, so that as the sponge or brush sweeps across the protective coating and comes into the vicinity of a holiday, electrolytic fluid can flow into the holiday and to the electrically grounded metal of the base plate and close the circuit, with the resulting spark or current flow that is registered by the controller.

Some holiday detection in liquid petroleum storage tanks has been done manually by persons who enter the tank and move a sponge apparatus along the surface of the base plate. This must be followed up directly by marking the location of the holiday with an ink stamp or other marking indicator suitable for material environment, and subsequent repair of the coating in a separate operation.

The environment inside liquid petroleum storage tank is both unpleasant and dangerous for humans because of the residual liquid petroleum fumes that are inhospitable for breathing and present a danger of fire and explosion.

Holiday testing apparatus can be used for example with a low-voltage wet sponge test for determining the existence of discontinuities in coating films having a total thickness of 0.5 mm or less. High-voltage spark test equipment is generally used for determining the existence of discontinuities in coating films having a total thickness of greater than 0.5 mm.

The fluid media, water or electrolytic fluid in the wet sponge fills the voids in the surface to be tested and allows low current to flow into any holidays in the test area. The current moves through the holiday and into the conductive substrate which activates a horn, light or other output to indicate the presence of the holiday.

The prior art includes manual holiday detection by humans carrying and operating holiday detection apparatus, and holiday detection apparatus carried by vehicles on tracks or within a pipe where the vehicle moves only in a straight path along which there are no obstacles to movement and thus no need to identify and avoid obstacles. Thus, conventional prior art holiday detection vehicles travel involve no concern or possibility for the vehicle to be turning, zigzagging, or even following parallel and/or overlapping paths.

The following U.S. patents disclose some of the above-mentioned prior art concepts and are incorporated herein by reference: U.S. Pat. Nos. 6,832,183, 3,106,677, 4,946,570 and 7,285,203.

III. SUMMARY AND OBJECTS OF THE NEW INVENTION

The present invention relates to a method and apparatus for detecting holidays in a protective coating on the metal surface, and particularly detecting and repairing holidays in a base plate of a liquid petroleum storage tank that is in a remote location where visual inspection and repair operations are difficult or impossible. This invention presents apparatus and a method for detecting and repairing holidays that is automatic, efficient and avoids the difficulties and of danger mentioned above in regard to humans conducting of such operations. In particular, the present application is for a low voltage wet sponge holiday testing apparatus for coating thickness of 20 mls (0.5 mm) or less. The new robotic vehicle can traverse a path on the surface of the base plate and cover substantially the entire area without missing spots and mark the holidays upon detection. Furthermore, the new robotic vehicle can be programmed to conduct its movements and marking automatically without requiring direction, attention and monitoring by a human.

An object of the present invention is to provide a method and apparatus for locating and marking holidays in the floor of a storage tank for liquid hydrocarbon fluids, which is an area and environment awkward or dangerous for human movement due to the residual hydrocarbon fumes, the constrained and closed area and various structural and functional apparatus in said area. This invention provides a robotic vehicle that can traverse a path or paths that cover the floor area in question, locate and mark holidays for repair, while being generally not constrained by factors that would apply to humans.

A further object is for such robotic vehicle while traveling to be able to deal with obstacles and with walls at the end of any pass, and to do so automatically and efficiently. Accordingly, it is an object for the vehicle to sense the presence of the obstacle or wall, move laterally to avoid the object, and return to forward or optionally rearward motion.

A still further object is for the vehicle when traversing parallel and adjacent passes to make sure the wiping sponges traverse overlapping paths so that no area is left un-wiped by the sponge containing electrolytic fluid.

An additional object is to include a set of wetting sponges that are aligned transversely of direction of motion, and electrically insulated from each other so that when a holiday is detected beneath one particular sponge, that specific location can be signaled to the controller which can maneuver and re-position the vehicle until its holiday marking unit is directly above the holiday to be marked. A variation would be for the controller to direct the holiday marking unit to establish a mark adjacent the detected holiday without moving the vehicle.

These and other objects will be evident from the drawings and description herein.

Various exemplary embodiments of the present invention are summarized below.

1. A robotic holiday testing apparatus for detecting and marking holidays in the protective coating atop a metal base plate of a storage tank, comprising:
   a. a vehicle having front, rear, left and right parts,
   b. a first set of wheels mounted to said vehicle such that the bottoms of said first set of wheels lie at a first elevation below said vehicle for enabling said vehicle to roll in the forward and rearward directions,
   c. a second set of wheels mounted to said vehicle such that the bottoms of said second set of wheels lie at a start elevation higher than said first elevation for enabling said vehicle to roll in the left and right directions,
   d. a power drive unit selectively coupled:
      i. to said first set of wheels to move said vehicle in the forward or backward direction, and ii. to said second set of wheels to move said vehicle and the right or left direction,
c. an elevator unit for selectively:
  i. lowering said second set of wheels so that the bottoms of said second set of wheels lie at a third elevation lower than said first elevation, whereby said first set of wheels is elevated off the base plate, and said second set wheels will engage said base plate and said vehicle is movable in said left and right directions, and
  ii. subsequently elevating said second set of wheels at least until said first set of wheels re-engages said base plate,
f. a holiday detection apparatus having a wettable sponge electrical contact element for establishing an electric circuit with the base plate through each of said holidays,
g. a tank for containing an electrolytic fluid supplied into said wettable sponge, and
h. a controller which selectively operates said power drive unit to:
  i. move said carriage on said first set of wheels in the forward direction for selected distance, and
  ii. lower said second set of wheels to contact said base plate and elevate said first set of wheels out of contact with said base plate, and
  iii. move said vehicle in the left or right direction for selected distance, and
  iv. elevate said second set of wheels out of contact with said base plate, until said first set of wheels regains contact with said base plate,
said vehicle thus being movable along a path while said holiday testing apparatus thereon detects and marks holidays for subsequent repair.

2. The apparatus according to embodiment 1 above further comprising a cleaning unit carried by said vehicle for cleaning said base plate ahead of movement of said vehicle.

3. The apparatus according to embodiment 2 wherein said cleaning unit comprises an air suction device.

4. The apparatus according to embodiment 1 further comprising at least one sensor for detecting obstacles in the path of movement of said vehicle and sending an alert signal to set controller.

5. The apparatus according to embodiment 4 where said sensor is a proximity sensor.

6. The apparatus according to embodiment 1 further comprising a cleaning unit carried by said vehicle for cleaning said base plate ahead of movement of said vehicle, and at least one sensor for detecting obstacles in the path of movement of said vehicle and sending an alert signal to said controller.

7. The apparatus according to embodiment 1 wherein said at least one wettable sponge of said holiday testing apparatus comprises a plurality of said sponges electrically insulated from each other.

8. The apparatus according to embodiment 7 where said plurality of sponges are spaced apart from each other but situated to define an uninterrupted path extending transversely of the forward or backward motion of the vehicle.

9. A robotic holiday testing apparatus for detecting and marking holidays in the protective coating atop a metal base plate of a storage tank, comprising:
a. a vehicle having front, rear, left and right parts,
b. a first set of wheels mounted to said vehicle such that the bottoms of said first set of wheels lie at a first elevation below said vehicle for enabling said vehicle to roll in the forward and rearward directions,
c. a second set of wheels mounted to said carriage such that the bottoms of said second set of wheels lie at a start elevation higher than said first elevation for enabling said vehicle to roll in the left and right directions, d. a power drive unit selectively coupled:
  i. to said first set of wheels to move said vehicle in the forward or backward direction, and
  ii. to said second set of wheels to move said vehicle and the right or left direction,
c. an elevator unit for selectively:
  i. lowering said second set of wheels so that the bottoms of said second set of wheels lie at a third elevation lower than said first elevation, whereby said first set of wheels is elevated off the base plate, and said second set of wheels will engage said base plate and said vehicle is movable in said left and right directions, and
  ii. subsequently elevating said second set of wheels at least until said first set of wheels re-engages said base plate,
d. a holiday detection apparatus having a wettable sponge electrical contact element for establishing an electric circuit with the base plate through each of said holidays,
e. a controller which will selectively operate said power drive unit to:
  i. move said vehicle on said first set of wheels in the forward direction for selected distance,
  ii. lower said second set of wheels to contact the base plate and elevate said first set of wheels out of contact with said base plate,
  iii. move said vehicle in the left or right direction for a selected distance, and
  iv. elevate said second set of wheels out of contact with said base plate, until said first of wheels regains contact with said base plate,
said vehicle thus being movable along a path while said holiday testing apparatus thereon detects and marks holidays for subsequent repair.

10. A robotic holiday testing apparatus for detecting and marking holidays in the protective coating atop the metal base plate of a storage tank, comprising:
a. a vehicle having front, rear, left and right parts,
b. a power drive unit selectively adapted to move said vehicle in the forward or backward direction, and to move said vehicle and the right or left direction,
c. a holiday detection apparatus having a wettable sponge electrical contact element for establishing electric circuit with the base plate through each of said holidays,
d. and a controller which selectively operates said power drive unit to:
  i. move said vehicle and the forward direction for a selected distance,
  ii. move said vehicle in the left or right direction for selected distance,
said carriage thus being movable along a path while said holiday testing apparatus thereon detects of marks holidays for subsequent repair.

11. The apparatus of embodiment 10 further comprising a cleaning unit carried by said vehicle for cleaning said base plate ahead of movement of said vehicle and at least one sensor for detecting obstacles in the path of movement of said carriage and sending an alert signal to said controller.

IV. BRIEF DESCRIPTION OF THE DRAWINGS

Figure 4:
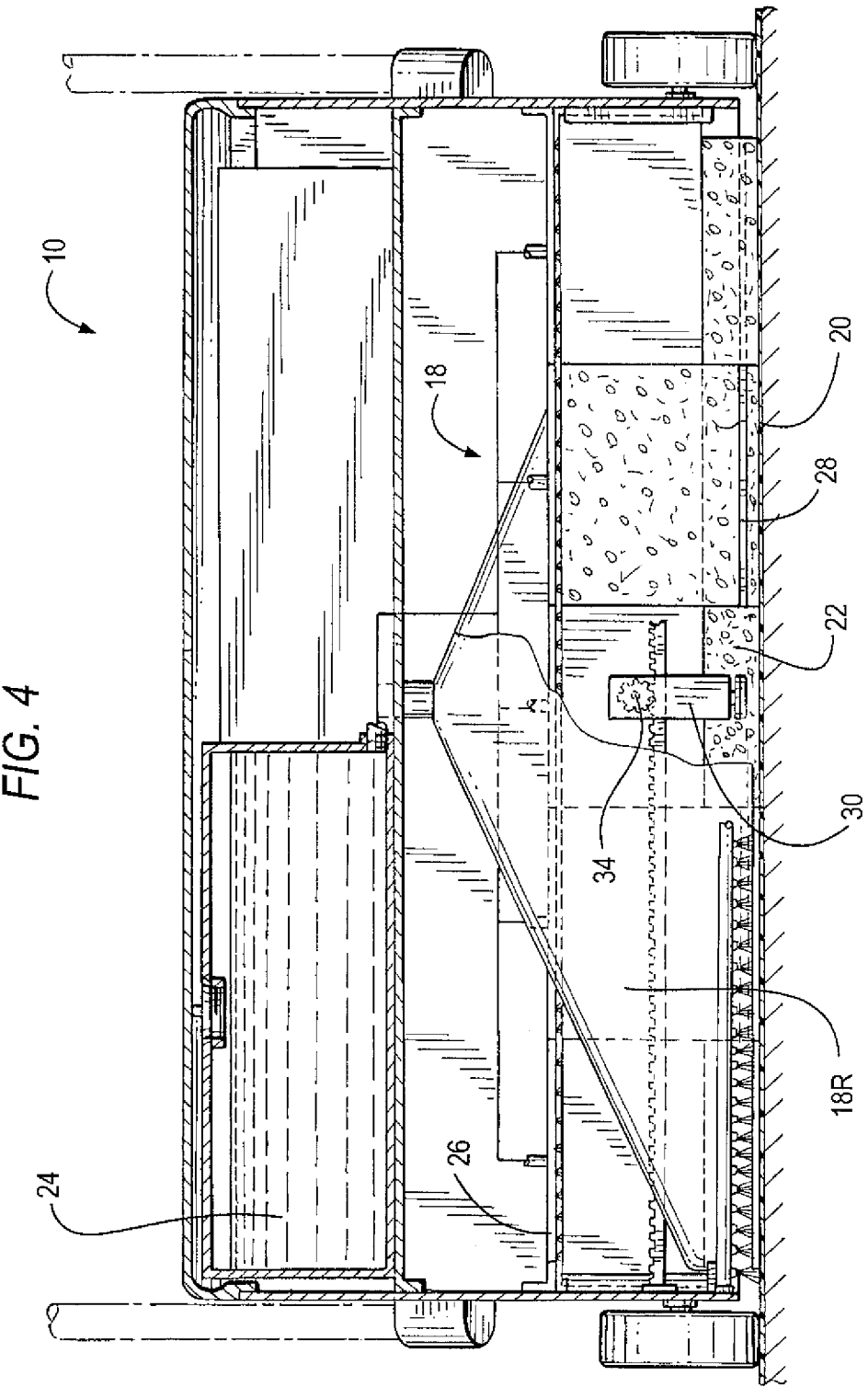
Figure 7:
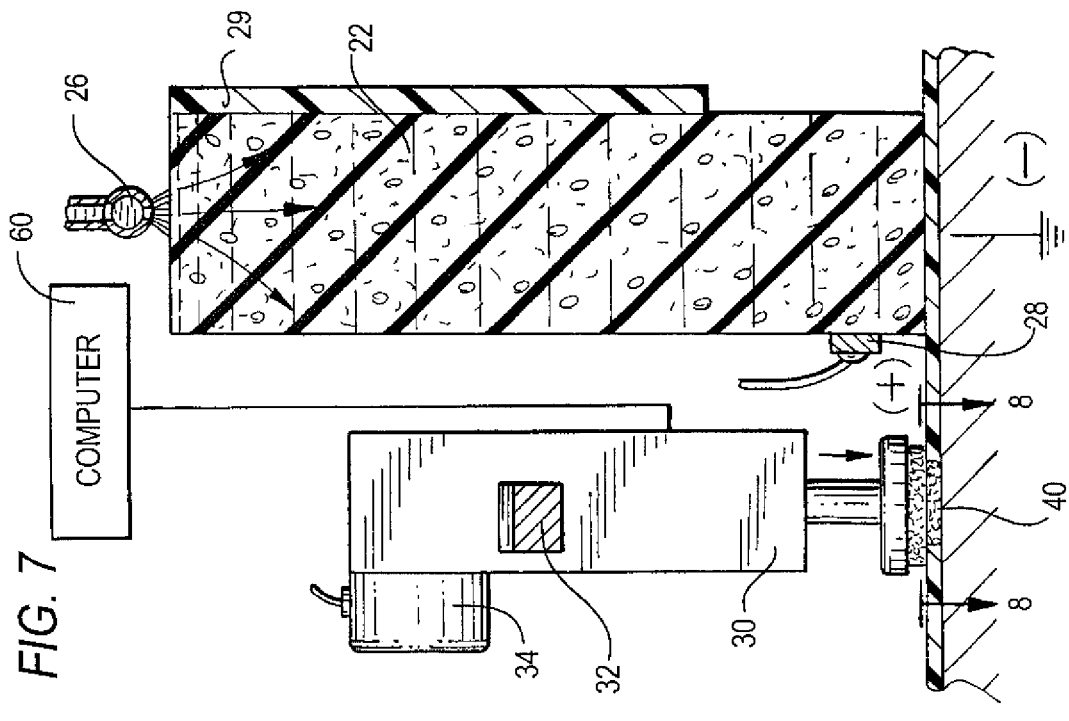
Figure 6:
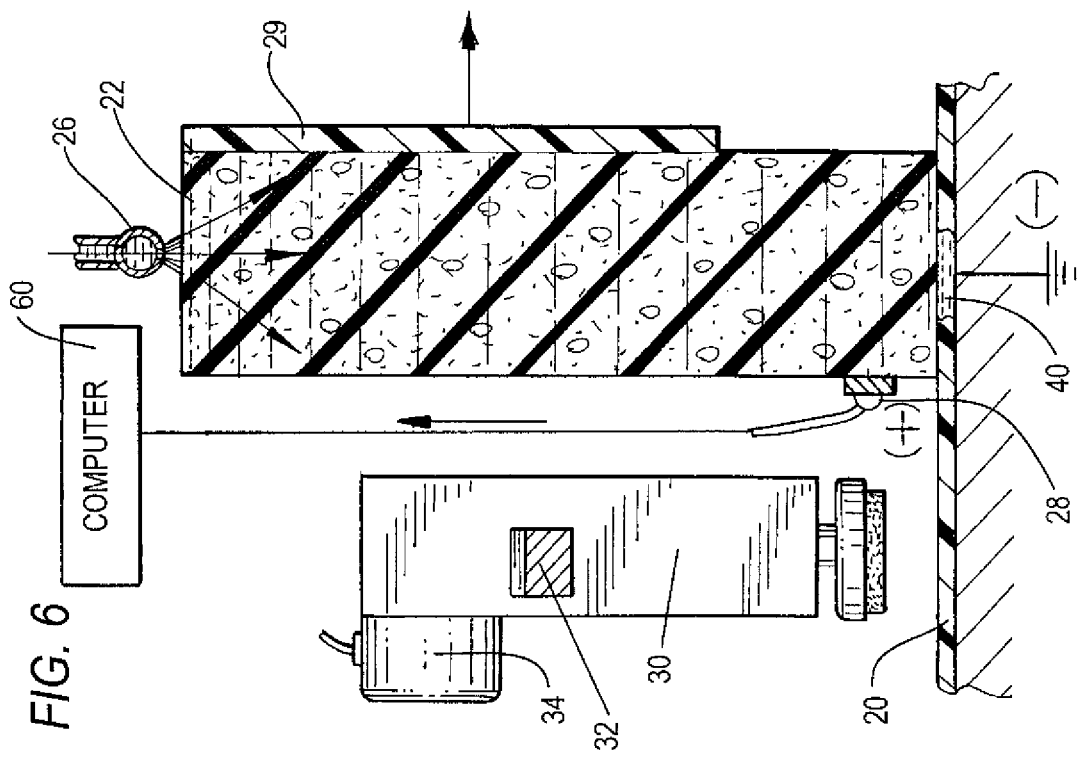
Figure 15:
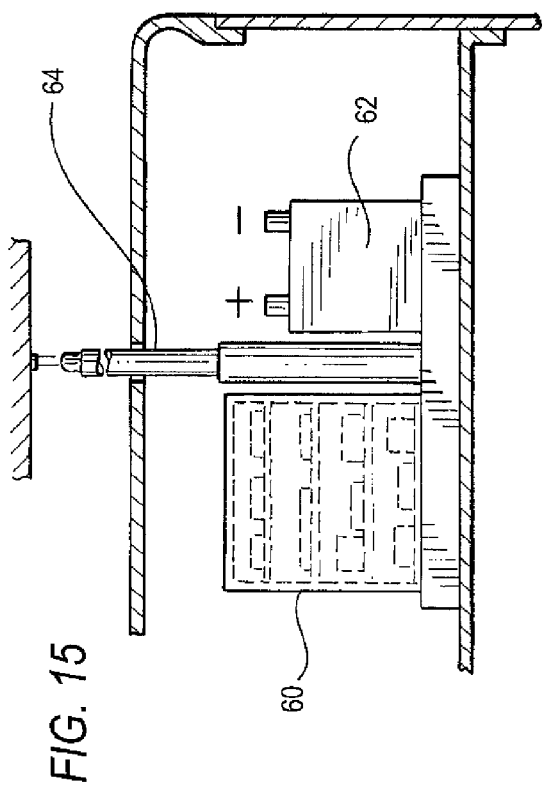
Figure 16:
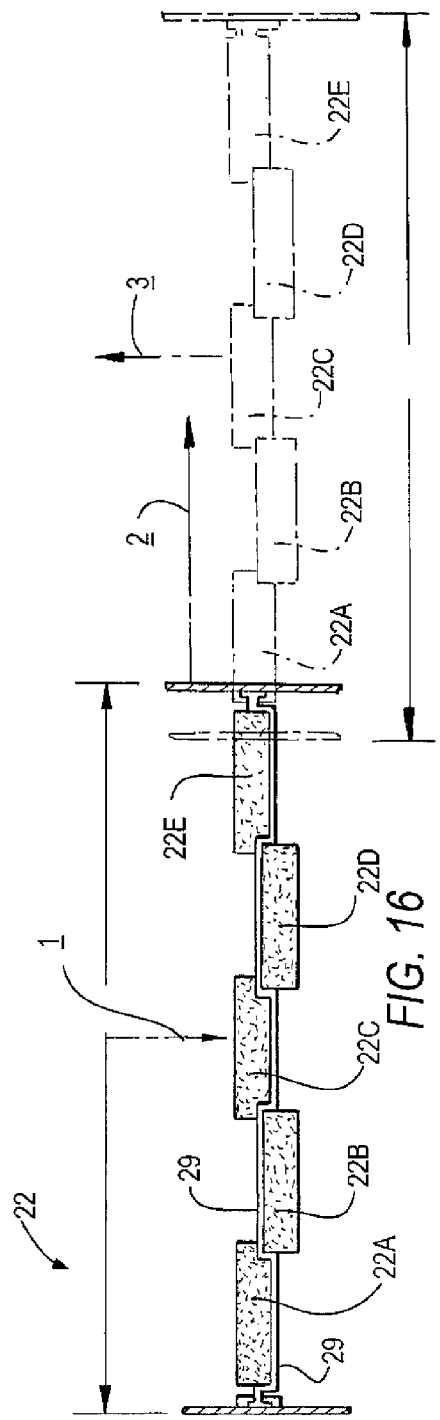
Figure 17:
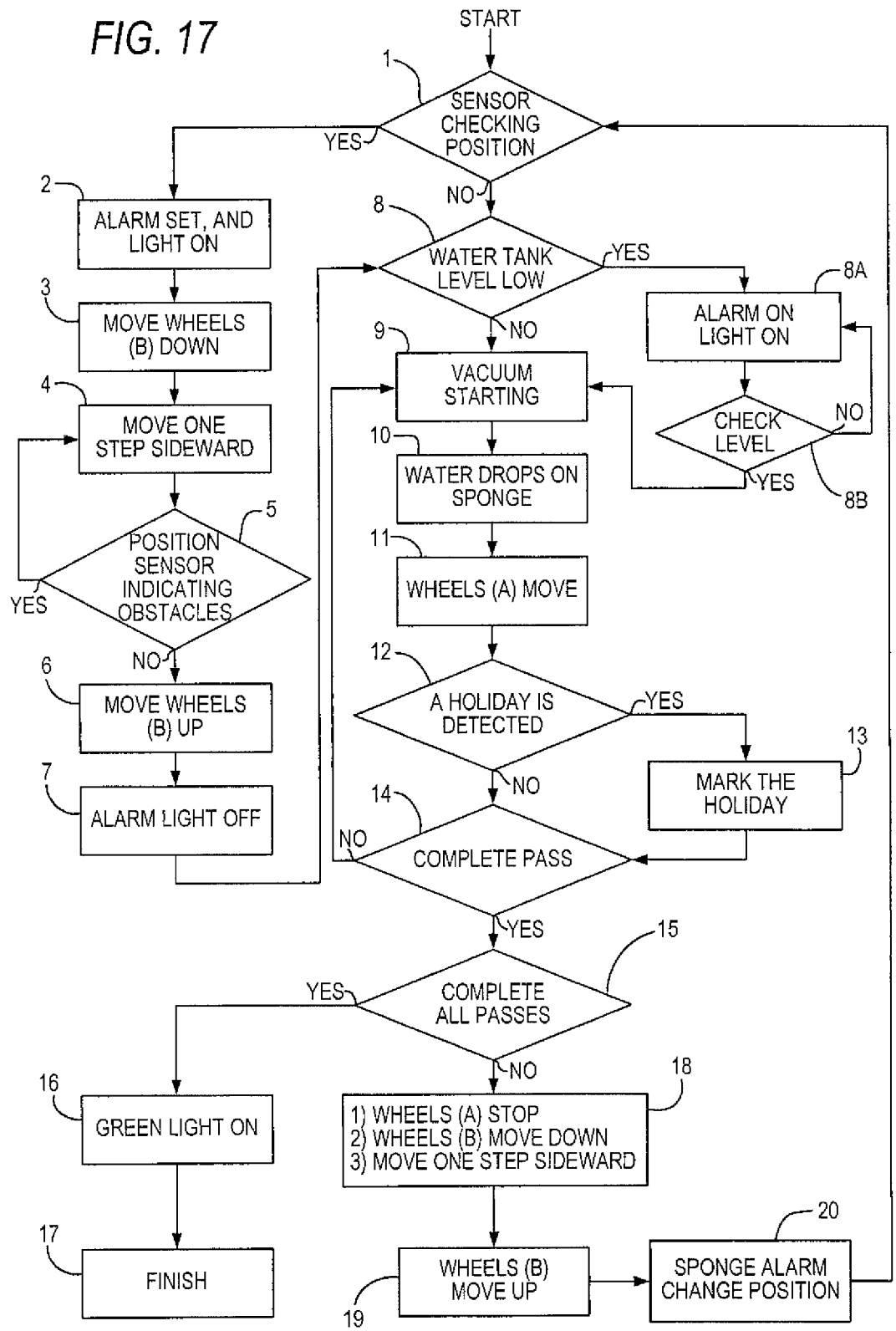

FIG. 1 is a top front perspective view of the new robotic vehicle for holiday testing, FIG. 2A is a top plan schematic view of a path of motion of the robotic vehicle for the major area of a storage tank base plate, FIG. 2B is a schematic view showing a portion of one path of motion of the robotic vehicle, FIG. 3 is a sectional plan view taken along line 3-3 in FIG. 1 showing the robotic vehicle including A wheels for forward and backward motion, and B wheels be for left and right motion, FIG. 4 is a sectional elevation view taken along line 4-4 in FIG. 3, FIG. 5 is an enlarged fragmentary sectional elevation view taken along line 5-5 in FIG. 3, FIG. 6 is an enlarged fragmentary view partially in section showing the sponge with electrolytic solution wiping the base plate in the vicinity of a holiday and the adjacent marking unit, FIG. 7 is similar to FIG. 6 but shows the vehicle having moved forward so that the marking unit is directly above the holiday and the marking unit has moved down to mark the holiday, FIG. 8 is a fragmentary top plan view taken along line 8-8 in FIG. 7 showing the holiday as marked by the marking unit, FIG. 9 is an elevation view taken along line 9-9 in FIG. 1 showing the B wheels in an elevated position, while the A wheels are in contact with the base plate, FIG. 10 is a fragmentary sectional elevation view taken along line 10-10 in FIG. 9 showing one of the B wheels and its drive motor, FIG. 11 is a fragmentary sectional plan view taken along line 11-11 in FIG. 9 further showing a B wheel and the link arm for elevating and lowering the B wheels, FIG. 12 is an elevation view similar to FIG. 9 showing the B wheels lowered to contact the base plate for left to right motion, with the A wheels being elevated, FIG. 13 is a fragmentary elevation sectional view taken along line 13-13 in FIG. 12, FIG. 14 is a fragmentary top plan view showing the link arms coupled to the B wheels shown in FIGS. 12 and 13, FIG. 15 is a fragmentary elevation sectional view taken along line 15-15 in FIG. 3, FIG. 16 is a fragmentary schematic top view of the sponges shown in FIG. 3 and their overlapping relationship to each other during movement of the vehicle, FIG. 17 is a flow chart showing the sequence of operational steps of an embodiment corresponding generally to the embodiment shown in FIGS. 1-16, FIG. 18 is a top front perspective view of another embodiment of the present invention, FIG. 19 is a top plan view of the embodiment of FIG. 18.

Figure 20:
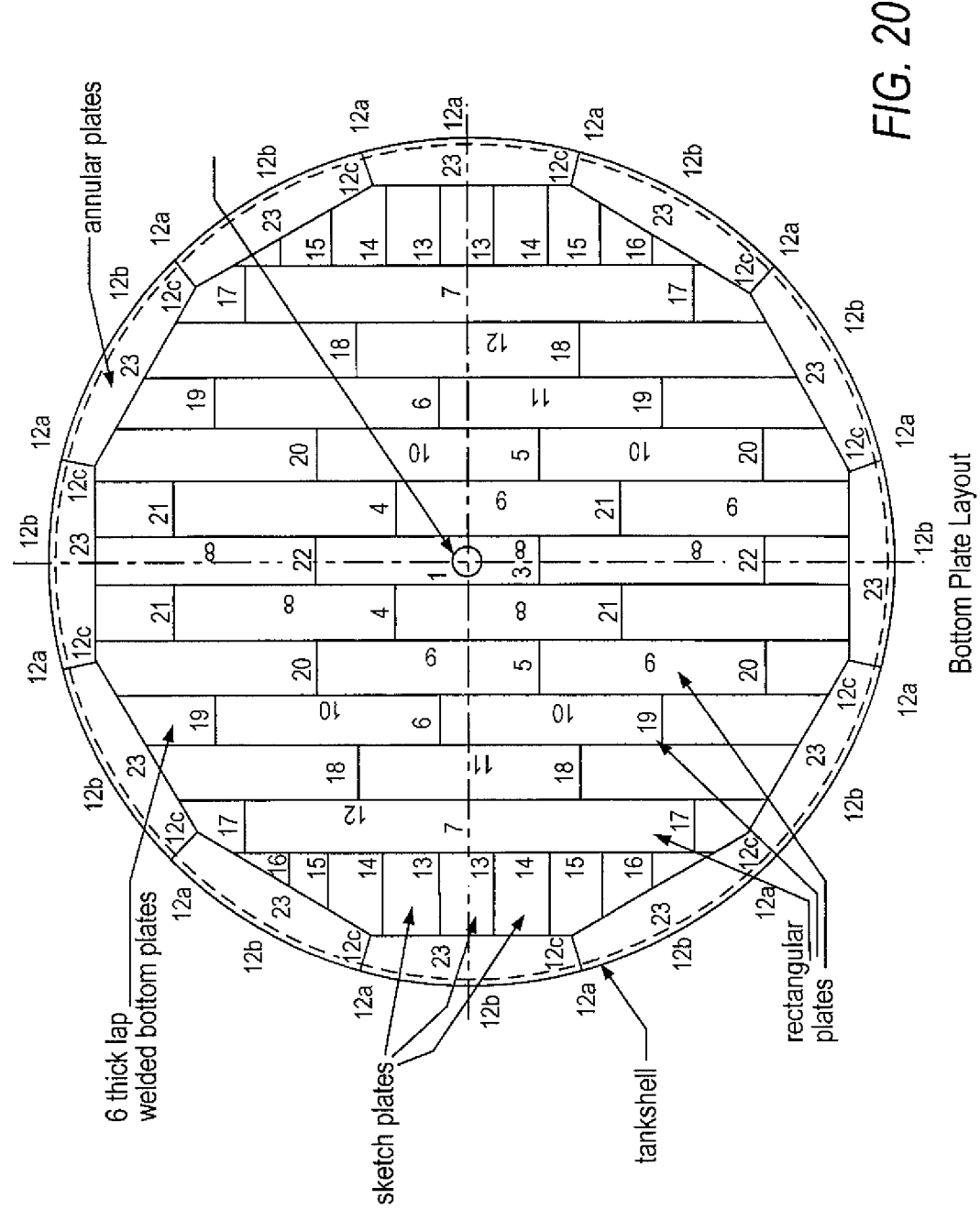
Figure 21:
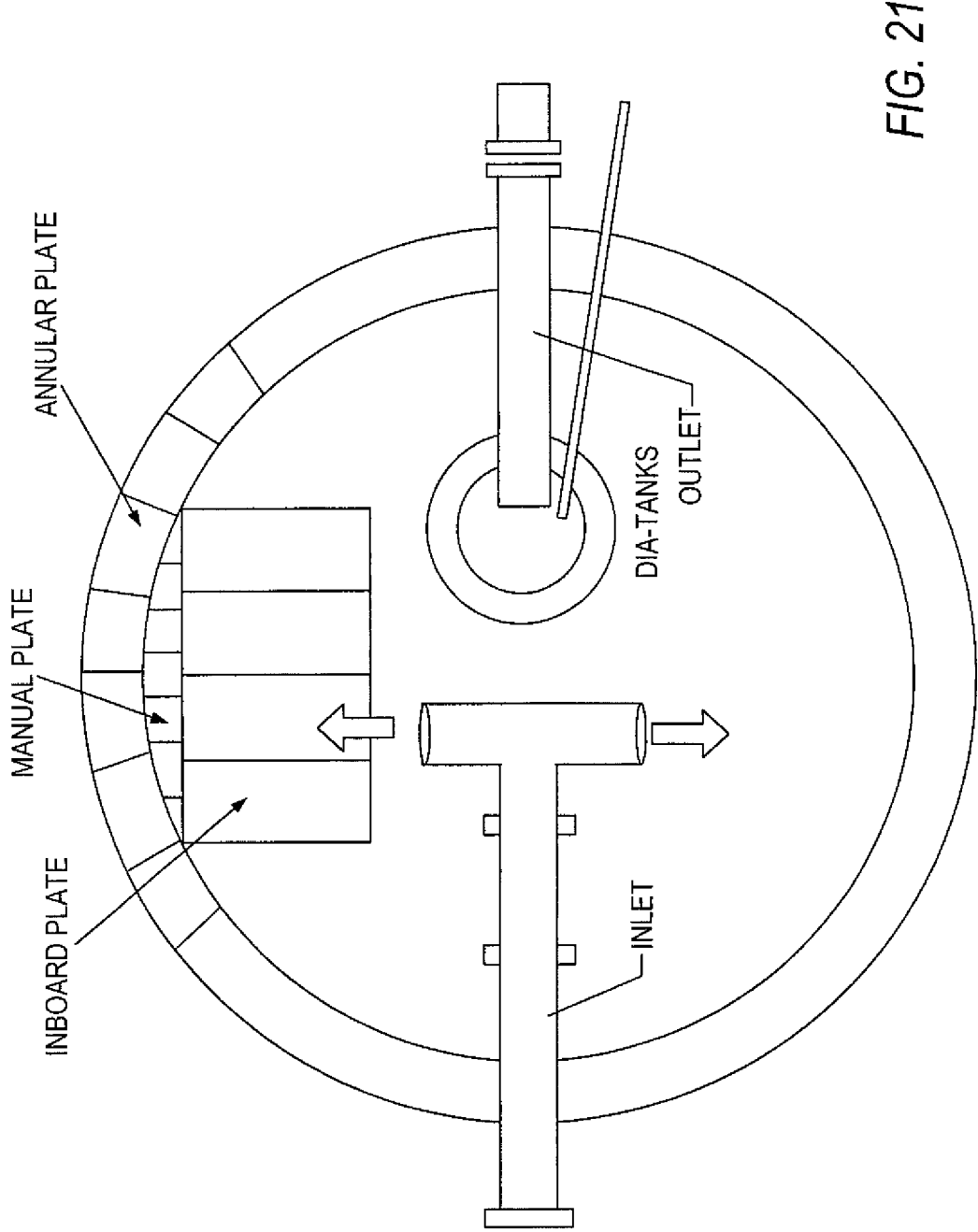

FIG. 20 is a top plan view of a metal plate arrangement on a floor of an exemplary fluid storage tank, and FIG. 21 is a schematic plan view of an exemplary fluid storage tank snowing inlet and outlet ducts and representative metal floor plates.

V. DETAILED DESCRIPTION OF THE PREFERRED EMBODIMENTS

For convenience and clarity in describing these embodiments, similar elements or components appearing in different figures will have the same reference numbers.

FIG. 1 shows schematically the outer housing of a robotic vehicle 10 for holiday testing of coatings on storage tank base plates. On the opposite sides 11 of the vehicle are the A wheels (also designated "wheels 12") for forward and rearward movement of the vehicle. On the front and rear sides 13 are the B wheels (also designated "wheels 14") for left and right movement of the vehicle. Other details of the structure and operation of the vehicle will be described in paragraphs and figures below.

FIG. 2A is a schematic view showing a possible path of travel 16 by the vehicle on an entire base plate within the side walls 17 of a storage tank. For simplicity this schematic path includes no path deviation for obstacles which are likely to be present. This area marked 16A (see enlarged drawing FIG. 2B) indicates how the vehicle moves from one pass to the next adjacent pass.

FIG. 2B shows schematically an enlarged view of the portion 16A of the path of travel of the vehicle, which moves for example from position a forward to position b, then to the right to position c, then rearward to position d continuing to position e, and then in the right direction to position f and then again forward to position g. In the manner shown the vehicle of this embodiment can traverse a large area of the base plate without having to turn and without having complex mechanisms and controls to cause such turns.

Briefly stated the function of the robotic vehicle described herein is to move along a path on the surface of the base plate of a storage tank and to investigate and discover holidays, namely the defects or holes in the coating on the surface of the base plate, and to mark each holiday with an ink stamp or other indication, for that area to be remedied as by repair or re-coating. This robotic vehicle has a variety of components which serve different functions, namely a vacuum or cleaning unit which may include a solvent spray for cleaning the area that is being approached by the vehicle in its path of movement. Next on the vehicle, adjacent and behind the cleaning unit is an arrangement of sponges and a supply of electrolytic solution directed into the sponges which sweep along the surface of the base plate, the sponges wetting said surface with the electrolyte for better electrical conductivity in the holiday detection phase. The sponges are arranged in an overlapping pattern as further described below, so that no area of the base plate remains un-wiped. To make electric connection with the base plate there are electrodes (electrical contacts or contact strips) coupled to the sponges. Also the vehicle carries a battery power source or uses an alternate power source, which is coupled to the above-mentioned contact strips. Next, as the vehicle moves and the sponges wipe the base plate, and electrolytic fluid flows from the sponge into any holiday and down to the metal base plate. A voltage potential exists between the contacts, through the electrolytic fluid to the base plate which establishes a spark or other evidence of circuit closure any time a wetted sponge encounters a holiday. With the current flow through the holiday gap in the coating to the metal of the base plate below, the computer controller identifies the location of this incident and directs an on-board marking unit to apply a mark or other indicia to that location on the base plate. For such marking the vehicle will move until the marking unit is directly above the detected holiday. The various structures and functions summarized above will now be described in further detail.

Vacuum Pick-up Unit 18 as illustrated in FIGS. 3, 5 and 5: It is assumed in these figures that forward motion is indicated by the arrow F and rearward motion by the arrow R. Vacuum pick-up unit 18 comprises an elongated pickup head 18F for the forward direction and elongated pick-up head 18R are for rearward direction. FIG. 5 shows an end elevation view of the vacuum pickup heads 18F and 18R having inlet openings 19F in 19R respectively directed to and closely adjacent the base plate 20. When the robotic vehicle moves forward in the direction of arrow F as seen in FIG. 3, the forward vacuum pickup head 18F cleans the area of the base plate 20 that is about to be approached by the sponges 22. Similarly when the robotic vehicle moves in a rearward direction indicated by arrow R in FIGS. 3 and 5, the rear vacuum pickup head 18R is activated to clean the area of the base plate 20 that is being approached by the vehicle.

Electrolytic sponges 22: As seen in FIGS. 3-7 and 16 the vehicle carries a set of five sponges 22a-22e whose ends are situated to slightly overlap each other, so that for example, when the vehicle is moving in the forward direction, the right end of sponge 22a is overlapped by the left end of sponge 22b to ensure that there is no area missed by sponges aligned from left to right. Cooperating with the sponges is a tank 24 of electrolytic fluid seen in FIGS. 4 and 5, which fluid is directed to the sponges 22. Also seen in FIGS. 3, 4 and 5 are contact elements 28, each attached to a sponge to ensure a reliable electrical circuit closure between the electric source, through the sponge, through the holiday to the grounded base plate. FIG. 16 also shows schematically how the vehicle can move forward per arrow 1, then sideward per arrow 2, then forward again per arrow 3. This forward, sideward, rearward path could occur when the vehicle has arrived at a storage tank wall and begins a new pass in the opposite direction. Alternatively, the vehicle could move forward, move sideward because of an obstacle, and then continue forward again.

Holiday marking units 30 as seen in FIGS. 3, 4 and 5 and later in FIGS. 6, 7 and 8: As mentioned above, when a holiday is detected at a location corresponding to one of the sponges, a corresponding signal is sent to the controller 60 (FIGS. 3, 6 and 7). As seen in FIG. 3, for example and assuming the vehicle is moving in the rear direction of arrow R, when a holiday is detected the vehicle then moves slightly further in the rear direction, and the marking unit 30 is moved transversely along a gear drive rack 32 until it is located above said detected holiday. The controller 60 then directs the marking unit 30 to apply an ink or other marking at that spot, by causing the marking unit to descend by a solenoid or other method. After marking unit 30 rises and the vehicle can continue to find other holidays. The use of ink stamping to mark holidays is often preferred since the ink marks can be easily erased when the holiday repair work is completed.

FIG. 6 illustrates more specifically how the sponge 22 and its contact element 28 may be positioned directly over a holiday 40 with the marking unit 30 still elevated, and FIG. 7 illustrates how the vehicle has moved until the unit 30 is directly above said holiday 40 and the marking unit has descended to apply its mark.

Vehicle's forward and backward movement on A wheels, and alternatively left and right on B wheels: As shown in FIG. 3 the A wheels 12 are situated on the left and right sides of the vehicle. FIG. 9 shows that these A wheels 12 are in contact with the base plate 20 for forward and rearward direction motion of the vehicle, and the B wheels 14 are slightly elevated and out of contact with the base plate.

When the vehicle's controller determines that its forward (or rearward) travel should stop, and that the vehicle should move to the left or right, the controller directs an elevator drive unit 50 to lower the B wheels until they contact the base plate 20, and to lower these B wheels still further so that the A wheels 12 become elevated out of contact with the base plate (See FIG. 9). The elevator drive unit 50 is exemplified by a solenoid 51 seen in FIGS. 1, 9 and 12, coupled to link arms 52 which pivot about a pivot axis 53. When the solenoid drives the near arm segment 54 upward, the remote arm segment 55 is driven downward as seen in FIG. 12 where the B wheels 14 are now in contact with base plate 20 and the A wheels 12 are lifted out of contact with base plate 20. With this configuration the controller can now direct a drive stepping motor M12 to rotate at least one of the B wheels for driving the vehicle in the left or right direction. FIG. 11 shows a typical B wheel coupled to a reversible electric motor M12 that is activated selectively by said control means. FIG. 5 also illustrates the reversible electric stepping motor M12 coupled directly to a B wheel.

While the particular arrangement of alternate travel paths of the vehicle in the forward and backward and then left or right directions has been illustrated in FIGS. 2A and 2B for this particular embodiment, it is contemplated that other paths are possible, including turning of the vehicle either by wheels which turn, or for example by driving one right front wheel without driving the corresponding left or rear wheels, to effectuate a turn.

While the robot's basic travel paths are linear, moving forward, backward and sideways according to programming and direction changes from sensors, this drive mode can be turned off, allowing for manual mode direction for the vehicle to move to peripheral areas of the storage tank floor. Typical obstacles in the vehicle path include roof support legs, roof drain pipes, internal piping, namely inlet distribution pipes, outlet pipes from the tank, water draw-off pipe from the sump and the sump itself.

The paths traversed by the vehicle may be established by a computer program coordinated with the actual dimensional topography of the storage tank floor and obstacles thereon, with the proximity sensors directing overriding adjustments in travel according to obstacles, the proximity sensors providing alternate or supplementary direction for the travel paths. The bottom deck comprises a plurality of steel plates, each being identifiable and having known dimensions, orientation and positions by which the computer program can plan the vehicle's path as suggested in FIG. 20.

There are numerous other structural arrangements possible, instead of solenoid 51 and arms 52, for alternating the elevation of the A and B wheels, such as independent elevation units for the A wheels and the B wheels instead of having the single elevation unit for only the B wheels as shown in this illustrative embodiment.

FIG. 12 includes a switch 70 which is activated when the remote portion 55 of lever arm 54 descends pushing the B wheels into contact with the base plate. This could automatically disengage power to the A wheels or send a signal for other purposes to the controller.

Controller 60: The computer controller 60 is seen in FIGS. 3 and 15 is carried by the vehicle along with a battery power supply 62 and antenna 64. The controller as indicated earlier is interconnected with the stepping drive motors for the A and B wheels, the vacuum units 18, the electrolytic tank 24, sponges 22, the holiday contacts 28, the holiday marking units 30, and elevator drive unit 50. The specific sequence of steps will be discussed in further detail below, this arrangement representing both an apparatus and a method which is claimed herein. The function of the antenna installed on the robotic vehicle is to make contact between the negative terminal of the holiday tester and the storage tank body, which may be contact with the bottom of a floating roof at a height about four to four and a half feet from the floor of the storage tank to the bottom of the floating roof. In case the tank bottom to be tested has a cone roof or dome roof, a long ground wire would be employed to connect the negative terminal of the holiday tester to the tank grounding system outside the tanks.

The holiday sensing apparatus 28: In connection with this vehicle the holiday detecting concept and apparatus can be selected from various ones known in the art, which include closing an electrical circuit via an electrolytic fluid between an electric source, through the holiday to the grounded base plate or by magnetic or other sensing means.

Proximity Sensors 70: Additional components of this preferred embodiment vehicle are sensors 70 shown at the four corners of the vehicle in FIG. 3 and in numerous other figures. These are optical or other types of sensors to detect an obstacle or the tank wall in the path of the vehicle, and to sense the distance of the vehicle therefrom. The sensors are coupled to the controller which subsequently directs changes of travel of the vehicle for continued detecting and marking.

Vacuuming Cleaning; Solvent Cleaning: As previously described vacuum heads 19F are applied in the forward direction of the vehicle and 19R in the rearward direction. This cleaning may be augmented by spraying a liquid solvent from tank 80 via spray heads 81 as seen in FIG. 5.

The solvent cleaning is normally completed inside the tank on the tank bottom plates before commencing abrasive blasting and coating operations. With this procedure, another solvent cleaning is not required. However, the bottom plates need to be cleaned from dust or dirt to avoid interference with the holiday testing. Thus, in the preferred embodiment a vacuum unit is attached with vacuum head to clean the dust and/or dirt before the application of wet sponge on the new coating. A small amount of surfactant (detergent) is added with the water to be used for wetting the sponge. This surfactant will help to ease the movement of sponge on the bottom plate.

Sponge Insulation: As seen in FIGS. 3 and 16, sponges 22a-22e are electrically insulated from each other so that when a holiday is detected beneath a particular sponge the computer then directs movement of the marking unit to the lateral location of that sponge and forward movement of the vehicle to the longitudinal location of the detected holiday.

Drive Motors: Stepping drive motors for the B wheels can be adapted, for example, to move the vehicle a predetermined distance in left or right direction, so that when the vehicle makes the next forward or rearward move, the sponges will not have left a gap or un-examined path. Also, the stepping motors for the A wheels can be set for moving the vehicle predetermined distances forward and backward, or can simply move the vehicle until an obstacle or wall is detected. Other drive motors have been mentioned for the marking units coupled to gear tracks, and solenoids to drive the elevator unit and the marking unit. Still other power drive units operate the vacuum units, and the spraying of solvent to the spray heads. The electrolytic fluid may flow by gravity feed or be pumped.

FIG. 17 presents a diagrammatic flow chart that corresponds generally to the embodiment shown in FIGS. 1-16. The flow chart stages are illustrated in rectangle and diamond shaped Boxes numbered 1-20 as follows.

1. The holiday vehicle begins movement in the forward direction with its proximity sensors 70 alert to continuously check its position relative to obstacles and to the storage tank walls.

2. If no obstacle or wall the vehicle moves to Box 8 and is ready to scan for holidays. At Box 8 the tank of water or electrolytic fluid is checked; if okay, Box 9 shows that the vehicle's vacuum starts to clean the base plate surface in advance of the sponge.

3. At Box 10 water/electrolytic fluid drops or is pumped into the sponges so they will be ready to detect holidays.

4. Per Box 11 the vehicle begins to move forward on the A wheels.

5. Per Box 12, if a holiday is detected, go to Box 13 and mark said holiday. Also, per Box 12, if a holiday is not detected, go to Box 14 and continue as before with the procedure of Boxes 9-13.

6. Box 15 indicates that all passes along the desired path are complete. Then, per Box 16 the vehicle's green light is on indicating "finished" and then Box 17.

7. Returning to Box 1, if or whenever the proximity sensor 70 indicates an obstacle, the chart moves to Box 2 where an alarm light is on.

8. Per Box 3 the B wheels (for left/right movement) are lowered until the A wheels (for forward/backward movement) become elevated off the base plate surface.

9. Per Box 4 the vehicle moves sideward (transversely) a predetermined distance.

10. Per Box 5 the position sensor "looks" for obstacles. If none, go to Box 6, B wheels lifted so that A wheels can again move forward. If the sensor sees an obstacle, go back to Box 4.

11. Assume from Box 5, no obstacle and per Box 6, B wheels positioned up and A wheels positioned down; per Box 7, alarm light off since there are no obstacles. Next, go to Box 8 to begin (or continue) a standard pass checking for holidays and continue through Boxes 9-14, etc.

12. Returning to Box 15, if all passes are completed, "yes", go to Box 16 as described earlier; if not, the A wheels stop (forward motion stops), B wheels descend, vehicle moves left/right "one step" (a predetermined distance); then to Box 19 B wheels rise, A wheels regain contact with the base plate. Since all passes complete, the process could stop; however, at Box 20, the sponge is examined for condition of electrolytic fluid in preparation for next operation. If fluid level is okay go to Box 1 and ready for new operation. The flow chart of FIG. 17 is illustrative of the invention concept herein, but variations and also deletions or additions of steps are possible.

The embodiment 90 in FIG. 18 of the present robotic vehicle for holiday testing has certain similarity to the embodiment of FIGS. 1-17; however, it has only "A" wheels 12 for forward and rearward motion but no B wheels for transverse motion. Optimally, these A wheels can be adapted to turn the carriage 91 to follow a desired or predetermined path. This vehicle includes frame 91, A wheels 12, vacuum cleaner and solvent spray head 2, holiday detector 3 and its travel path shown by arrows 94, battery 95, solvent tank 96, proximity sensors 97, and direction of vehicle movement shown by arrow 98. With the apparatus as shown the holiday detecting apparatus provides an alarm signal, audible, electronic or otherwise when a holiday is detected.

FIG. 21 illustrates schematically inlet and outlet ducts for fluid in a storage tank, ad exemplary metal plates on the tank floor.

While the invention has been described in conjunction with several embodiments, it is to be understood that many alternatives, modifications, and variations will be apparent to those skilled in the art in light of the foregoing description. Accordingly, this invention is intended to embrace all such alternatives, modifications, and variations which fall within the spirit and scope of the appended claims.

The invention claimed is:

1. A robotic holiday testing apparatus for detecting and marking holidays in the protective coating atop a metal base plate of a storage tank, comprising:
   a. a vehicle having front, rear, left and right parts,
   b. a first set of wheels mounted to said vehicle such that the bottoms of said first set of wheels lie at a first elevation below said vehicle for enabling said vehicle to roll in the forward and rearward directions,
   c. a second set of wheels mounted to said vehicle such that the bottoms of said second set of wheels lie at a second elevation higher than said first elevation for enabling said vehicle to roll in the left and right directions, d. a power drive unit selectively coupled:
   i. to said first set of wheels to move said vehicle in the forward or backward direction, and
   ii. to said second set of wheels to move said vehicle and the right or left direction,
e. an elevator unit for selectively:
   i. lowering said second set of wheels so that the bottoms of said second set of wheels lie at a third elevation lower than said first elevation, whereby said first set of wheels is elevated off the base plate, and said second set wheels will engage said base plate and said vehicle is movable in said left and right directions, and
   ii. subsequently elevating said second set of wheels at least until said first set of wheels re-engages said base plate,
f. a holiday detection apparatus having a wettable sponge electrical contact element for establishing an electric circuit with the base plate through each of said holidays,
g. a tank for containing an electrolytic fluid supplied into said wettable sponge, and
h. a controller which selectively operates said power drive unit to:
   i. move said vehicle on said first set of wheels in the forward direction for selected distance, and
   ii. lower said second set of wheels to contact said base plate and elevate said first set of wheels out of contact with said base plate, and
   iii. move said vehicle in the left or right direction for selected distance, and
   iv. elevate said second set of wheels out of contact with said base plate, until said first set of wheels regains contact with said base plate,
   said vehicle thus being movable along a path while said holiday testing apparatus thereon detects and marks holidays for subsequent repair.

2. The apparatus according to claim 1 further comprising a cleaning unit carried by said vehicle for cleaning said base plate ahead of movement of said vehicle.

3. The apparatus according to claim 2 wherein said cleaning unit comprises an air suction device.

4. The apparatus according to claim 1 further comprising at least one sensor for detecting obstacles in the path of movement of said vehicle and sending an alert signal to set controller.

5. The apparatus according to claim 4 where said sensor is a proximity sensor.

6. The apparatus according to claim 1 further comprising a cleaning unit carried by said vehicle for cleaning said base plate ahead of movement of said vehicle, and at least one sensor for detecting obstacles in the path of movement of said vehicle and sending an alert signal to said controller.

7. The apparatus according to claim 1 wherein said at least one wettable sponge of said holiday testing apparatus comprises a plurality of said sponges electrically insulated from each other.

8. The apparatus according to claim 7 where said plurality of sponges are spaced apart from each other but situated to define an uninterrupted path extending transversely of the forward or backward motion of the vehicle.

9. A robotic holiday testing apparatus for detecting and marking holidays in the protective coating atop a metal base plate of a storage tank, comprising:
   a. a vehicle having front, rear, left and right parts,
   b. a first set of wheels mounted to said vehicle such that the bottoms of said first set of wheels lie at a first elevation below said vehicle for enabling said vehicle to roll in the forward and rearward directions,
   c. a second set of wheels mounted to said carriage such that the bottoms of said second set of wheels lie at a second elevation higher than said first elevation for enabling said vehicle to roll in the left and right directions,
   d. a power drive unit selectively coupled:
      i. to said first set of wheels to move said vehicle in the forward or backward direction, and
      ii. to said second set of wheels to move said vehicle and the right or left direction,
   e. an elevator unit for selectively:
      i. lowering said second set of wheels so that the bottoms of said second set of wheels lie at a third elevation lower than said first elevation, whereby said first set of wheels is elevated off the base plate, and said second set of wheels will engage said base plate and said vehicle is movable in said left and right directions, and
      ii. subsequently elevating said second set of wheels at least until said first set of wheels re-engages said base plate,
   f. a holiday detection apparatus having a wettable sponge electrical contact element for establishing an electric circuit with the base plate through each of said holidays,
   g. a controller which will selectively operate said power drive unit to:
      i. move said vehicle on said first set of wheels in the forward direction for selected distance,
      ii. lower said second set of wheels to contact the base plate and elevate said first set of wheels out of contact with said base plate,
      iii. move said vehicle in the left or right direction for a selected distance, and
      iv. elevate said second set of wheels out of contact with said base plate, until said first of wheels regains contact with said base plate,
      said vehicle thus being movable along a path while said holiday testing apparatus thereon detects and marks holidays for subsequent repair.

10. A robotic holiday testing apparatus for detecting and marking holidays in the protective coating atop the metal base plate of a storage tank, comprising:
    a. a vehicle having front, rear, left and right parts,
    b. a power drive unit selectively adapted to move said vehicle in the forward or backward direction, and to move said vehicle and the right or left direction,
    c. a holiday detection apparatus having a wettable sponge electrical contact element for establishing electric circuit with the base plate through each of said holidays,
    d. and a controller which selectively operates said power drive unit to:
       i move said vehicle in the forward direction for a selected distance,
       ii. move said vehicle in the left or right direction for selected distance, and
    e. a cleaning unit carried by said vehicle for cleaning said base plate ahead of movement of said vehicle and at least one sensor for detecting obstacles in the path of movement of said vehicle and sending an alert signal to said controller,
    said vehicle thus being movable along a path while said holiday testing apparatus thereon detects and marks holidays for subsequent repair.

11. A robotic holiday testing apparatus for detecting and marking holidays in the protective coating atop the metal base plate of a storage tank, comprising:
    a. a vehicle having front, rear, left and right parts,
    b. a power drive unit selectively adapted to move said vehicle in the forward or backward direction, and to move said vehicle and the right or left direction, c. a holiday detection apparatus having a wettable sponge electrical contact element for establishing electric circuit with the base plate through each of said holidays, d. a controller which selectively operates said power drive unit to:
  i. move said vehicle in the forward direction for a selected distance,
  ii. move said vehicle in the left or right direction for selected distance, and e. a cleaning unit carried by said vehicle for cleaning said base plate ahead of movement of said vehicle, said vehicle thus being movable along a path while said holiday testing apparatus thereon detects of marks holidays for subsequent repair.

12. A robotic holiday testing apparatus for detecting and marking holidays in the protective coating atop the metal base plate of a storage tank, comprising:

a. a vehicle having front, rear, left and right side parts, b. a power drive unit selectively adapted to move said vehicle in the forward or backward direction, and to move said vehicle and the right or left direction, c. a holiday detection apparatus having a wettable sponge electrical contact element for establishing electric circuit with the base plate through each of said holidays, and d. a controller which selectively operates said power drive unit to:
    i. move said vehicle in the forward direction for a selected distance,
    ii. move said vehicle in the left or right direction for selected distance, said power drive unit comprising a first set of wheels on said left and right sides of said vehicle for moving said vehicle forward and backward, and a second set of wheels on said front and rear sides for moving said vehicle in said left and right directions, said controller selectively drives either said first set of wheels were said second set of wheels, while lifting the set of wheels not being driven from contact with said base plate, said vehicle thus being movable along a path while said holiday testing apparatus thereon detects of marks holidays for subsequent repair.

13. A robotic holiday testing apparatus according to claim 12 where said first set of wheels comprises front and rear wheels on each side of said vehicle and said second set of wheels comprises left and right wheels on said front and rear sides of said vehicle.

* * * * *